United States Patent [19]
Wittig et al.

[11] Patent Number: 5,553,979
[45] Date of Patent: Sep. 10, 1996

[54] PULL CAP FOR ATTACHMENT TO A PROBE ROD

[75] Inventors: Volker Wittig, Salina; Melvin P. Kejr, Brookville, both of Kans.

[73] Assignee: Kejr Engineering, Inc., Salina, Kans.

[21] Appl. No.: 377,979

[22] Filed: Jan. 25, 1995

[51] Int. Cl.⁶ ............................... F02D 9/00; F21B 19/00
[52] U.S. Cl. .................... 405/232; 166/93.1; 254/29 R
[58] Field of Search ..................... 405/232; 254/29 R; 166/79.1, 93.1, 75.13

[56] References Cited

U.S. PATENT DOCUMENTS

| | | | |
|---|---|---|---|
| 836,065 | 11/1906 | Coates | 166/93.1 X |
| 5,154,537 | 10/1992 | McCown, Sr. et al. | 405/232 X |
| 5,375,664 | 12/1994 | McDowell et al. | 405/232 X |
| 5,377,768 | 1/1995 | Smith | 405/232 X |

OTHER PUBLICATIONS

Pages 2.3 and 2.4 of "Geoprobe Systems, 1993–1994 Equipment and Tools Catalog," and the pull caps depicted therein which were published, in public use or on sale in the United States prior to Jan. 25, 1994.

*Primary Examiner*—David J. Bagnell
*Assistant Examiner*—Frederick L. Laoman
*Attorney, Agent, or Firm*—Shook, Hardy & Bacon L.L.P.

[57] ABSTRACT

A pull cap is positioned about the exposed end of a probe rod and engages a pulling device to remove the probe rod from the ground. The pull cap has a first body section with a first concave surface disposed adjacent one end of the first section and for engaging the exposed end of the rod. The first body section also has a first channel on its outer surface adjacent the other end of the first section. A second body section has a second concave surface disposed adjacent one end of the second section and for engaging the exposed end of the rod. The second body section also has a second channel on its outer surface adjacent the other end of the second section. A hinge arrangement is disposed on both the first and second sections adjacent the other ends of the first and second sections. The hinge arrangement hinges the first and second sections together so that the pull cap has an open position and a closed position. The first and second concave surfaces engage the exposed end of the probe rod when the pull cap is in its closed position so that the pull cap can be used to remove the probe rod from the ground. An elastic member is positioned in the first and second channels and biases the pull cap into its closed position.

12 Claims, 2 Drawing Sheets

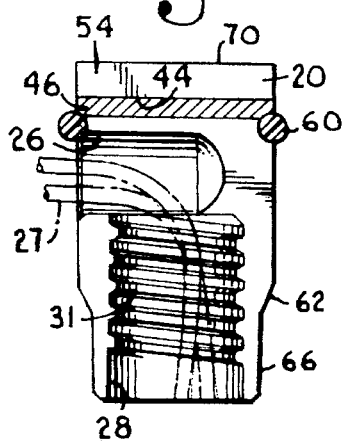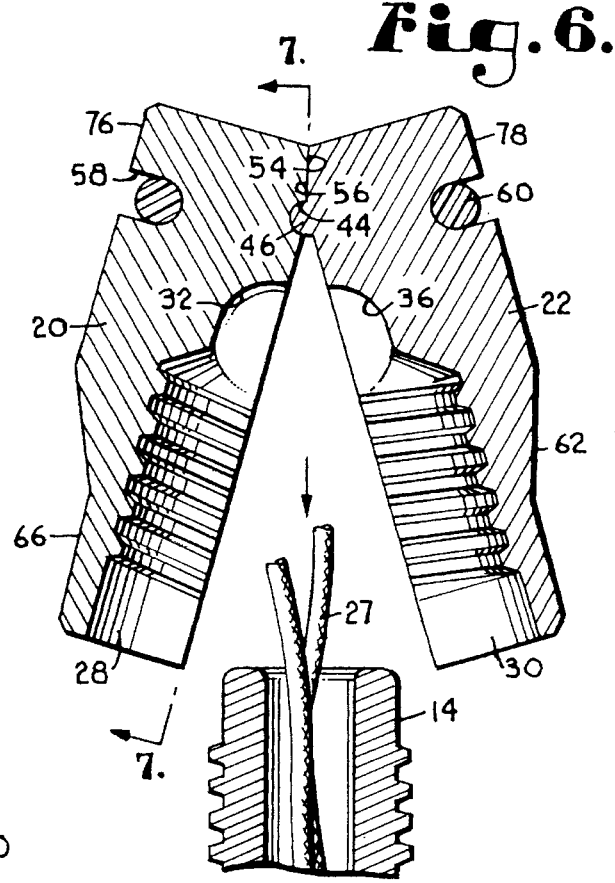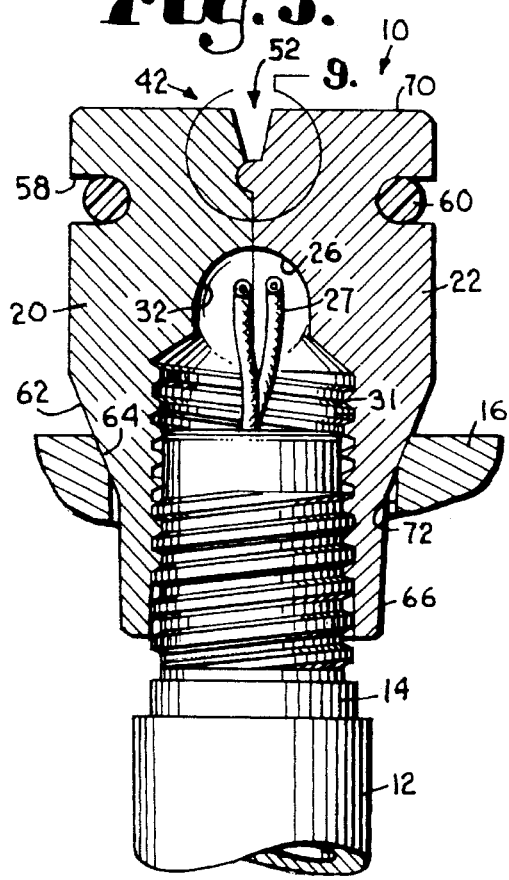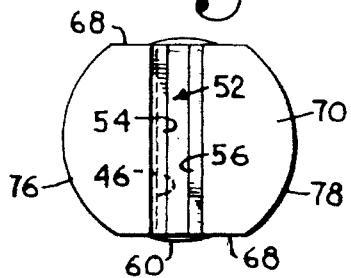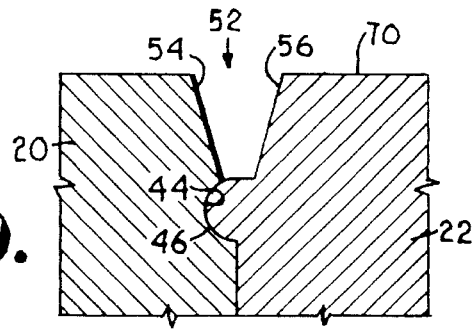

PULL CAP FOR ATTACHMENT TO A PROBE ROD

This invention relates to a cap that clasps the exposed end of a probe rod section in order to facilitate removal of a string of probe rod sections from the ground.

Recently, probing systems utilizing small diameter probes have been used increasingly for subsurface investigations. These probing systems typically utilize a percussion hammer to drive a probe into the ground. The probe is driven to a desired depth by utilizing a string of probe rod sections. A first probe rod section is attached to the probe and driven into the ground by applying percussive forces to the upper end of the rod section. After the rod section is driven into the ground, another rod section is connected to the exposed end of the first section and this second section is driven into the ground. Additional rod sections can be utilized in this manner until the probe is driven to a desired depth. The rod sections typically are connected together using a male/female thread arrangement. The upper end of a rod section has a male thread surface which mates with a female thread surface located on the lower end of the rod section above.

A percussion hammer used to drive a rod string into the ground is typically hydraulically driven. Further, the hammer is moved downwardly by a hydraulically driven cylinder. More specifically, after the hammer has applied percussive forces to the rod string and the rod string is driven a corresponding distance into the ground, the cylinder moves the hammer downwardly so that the hammer can again be in position to apply percussive forces to the upper end of the rod string.

After the probe reaches a desired depth, it is necessary to remove the rod string and the probe attached thereto from the ground. In order to do this, the hydraulic cylinder used to vertically position the hammer is utilized. More particularly, a pull cap is first threaded onto the exposed end of the rod string. This pull cap has a female thread surface which mates with the male thread surface of the exposed end of the rod string. The pull cap also has a generally annular horizontal flange extending outwardly from its exterior surface. This flange engages a generally C-shaped latch member that is attached to the cylinder. The latch member is capable of being pivoted between a stowed position and an operating position. In the operating position, the latch member engages the flange of the pull cap. After the latch member has engaged the pull cap, the cylinder is actuated upwardly so that the rod string is pulled partially from the ground. Thereafter at least one section of the rod string is removed. The pull cap is then positioned on the exposed end of the remaining rod string and the process is repeated until the entire rod string is removed from the ground.

As is apparent, the removal of the rod string from the ground is time consuming and labor intensive. More particularly, in order to remove each rod section from the ground, the drive cap must be threaded onto the exposed end of the rod section, the section pulled from the ground, and the pull cap removed from the section. Thus, the pull cap must be threaded on and off of each rod section that is removed.

In some of the soil probing systems used currently, each rod section has a hollow bore formed along its entire length. The bores of the rod sections are in communication with each other when the rod sections are connected together. Thus, instrumentation wires or tubes often are connected to the probe at the end of the rod string, extend upwardly through the central bores, and extend out the exposed end of the rod string. The wires or tubes are connected to an instrumentation device above ground so that soil data can be taken as the probe is driven downwardly. The wires or tubes interfere with the threading of a drive cap onto the end of the rod string. Thus, a conventional pull cap cannot be used when these instrumentation structures extend through a rod string.

In order to remove a rod string having instrumentation wires, a special pull plate is used. The pull plate is positioned around the rod section and binds the rod section at a location below the male thread surface located on the exposed end. A chain is hooked between the pull plate and a hook on the cylinder. The cylinder exerts an upward force on the pull plate via the chain. Because the pull plate is attached to an intermediate portion of the rod section instead of at its end, the pulling force applied to the rod by the cylinder via the chain is not in axial alignment with the rod string. This can result in unwanted torque on the rod string which can possibly damage or bend the rod sections.

Need has arisen for a pulling accessory which overcomes the foregoing deficiencies. The device of the present invention has been developed to fulfill this need.

Accordingly, it is a primary object of the present invention to provide a pull cap which can be easily attached to and removed from the exposed end of a probe rod string.

A further important object of this invention is to provide a pull cap that can accommodate a probe rod string that has a central bore with a wire or tube disposed in the bore.

A further object of the present invention is to provide a pull cap that can engage the threads on the exposed end of a probe rod string without having to be threaded onto the end.

A still further object of the present invention is to provide a pull cap that has a simple and easily manufactured hinge structure.

These and other important aims and objectives of the present invention will be described, or will become apparent from the following description and explanation of the figures, wherein:

FIG. 5 is an enlarged, detailed cross-sectional view taken generally along line 5—5 of FIG. 3, and showing the pull cap in its closed position clasping the end of the rod string and showing the pull cap engaging the latch member of the pulling device;

FIG. 6 is a detailed cross-sectional view similar to FIG. 5, but showing the pull cap in its open position so that it can receive the end of the rod string;

FIG. 7 is a detailed cross-sectional view taken generally along line 7—7 of FIG. 6;

FIG. 8 is a top plan view of the pull cap of the present invention; and

FIG. 9 is a fragmentary, enlarged cross-sectional view of the region indicated by the numeral 9 in FIG. 5.

Figure 1:
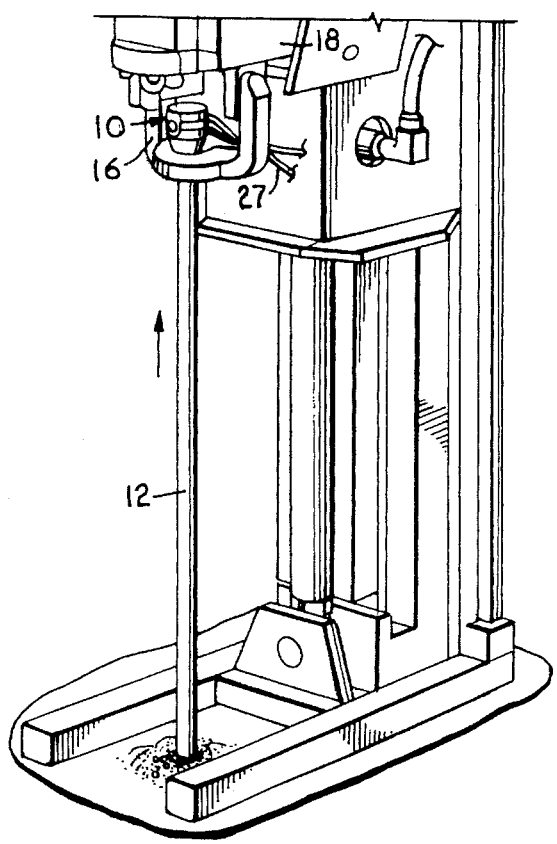
FIG. 1 is a fragmentary perspective view of a pulling device coupled with a pull cap embodying the principles of this invention, and showing the pull cap attached to the top of the rod string with a portion of the rod string removed from the ground.
Figure 2:
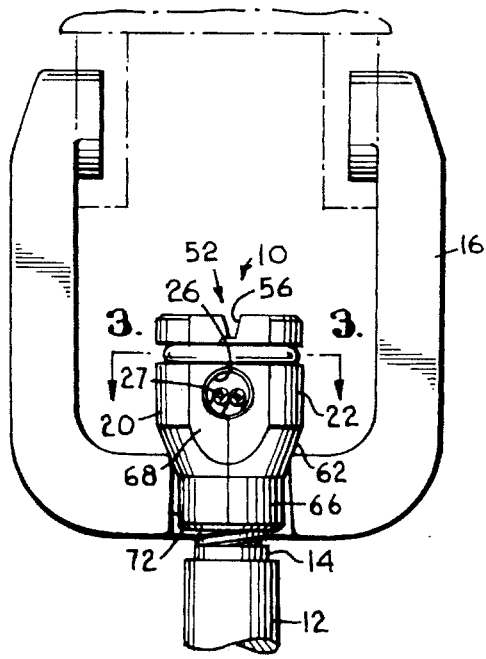
FIG. 2 is an enlarged rear elevational view of the pull cap shown in FIG. 1, and showing the pull cap attached to a rod and engaging the latch member of the pulling device.
Figure 3:
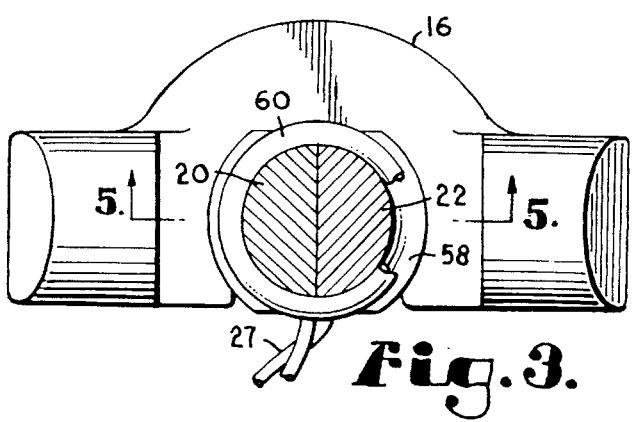
FIG. 3 is an enlarged, detailed cross-sectional view taken generally along line 3—3 of FIG. 2, parts being broken away to reveal details of construction.

A pull cap embodying the principles of this invention is broadly designated in the drawings by the reference numeral 10. Cap 10 engages and clasps a probe rod section 12 at an end 14 as best shown in FIGS. 2 and 5. Other rod sections are generally positioned below rod section 12. These other rod sections extend into the ground to form a rod string. A probe (not shown) is positioned at the lowermost end of the rod string. End 14 represents the exposed end of the rod string. A latch member 16 attached to a pulling device 18 engages cap 10 to allow the rod string to be moved upwardly so that rod section 12 is removed from the ground, as depicted in FIG. 1 and as will be more fully explained below. Rod section 12 is then detached from the rod string.

Figure 4:
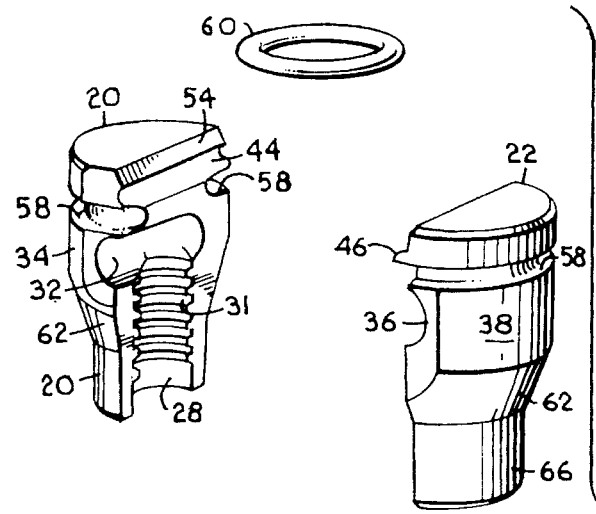
FIG. 4 is an exploded top perspective view of the pull cap of the present invention and of the latch member of the pulling device.
Figure 4:
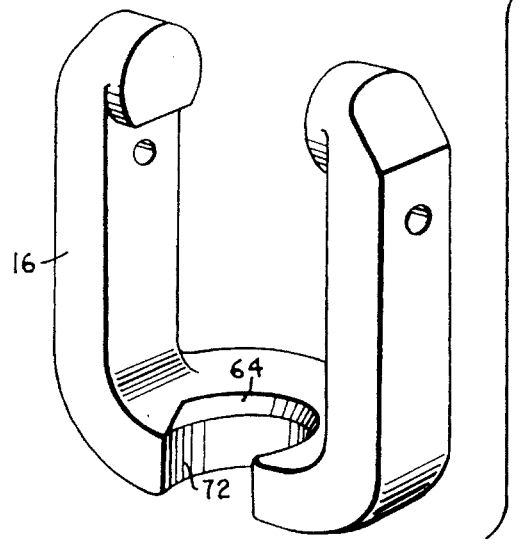

Cap 10 has a body section 20 and a body section 22 as best shown in FIGS. 4 and 6. Sections 20 and 22 cooperate with one another to clasp end 14 of rod section 12. Sections 20 and 22 are also configured and cooperate to form an aperture 26 extending laterally into cap 10 as best shown in FIG. 2. Aperture 26 allows cap 10 to accommodate wires or tubes 27 extending out of end 14, as will be more fully described below.

Section 20 has an inner concave surface 28 as best shown in FIGS. 4 and 6. Surface 28 has a portion of a female thread surface formed thereon. Section 22 has an inner concave surface 30. Surface 30 also has a portion of a female thread surface formed thereon. When cap 10 is in its closed position, as shown in FIG. 5, surfaces 28 and 30 cooperate to form bore 31. The partial female thread surfaces also align and cooperate to form a continual female thread surface that is adapted to clasp and engage the male thread surface on end 14 of rod section 12, as will be more fully described below.

Section 20 also has a lateral concave surface 32 which extends inwardly from an outer surface 34 of section 20 and connects with surface 28. Section 22 also has a lateral concave surface 36 which extends inwardly from an outer surface 38 of section 22 and connects with surface 30. When cap 10 is in a closed position, surfaces 32 and 36 form aperture 26 extending through the cap in spatial communication with the upper end of bore 31. Aperture 26 opens to the exterior surface of the cap as best shown in FIG. 5.

Cap 10 has a hinge arrangement 42 which allows the cap to pivot between its open and closed positions as shown in FIGS. 5 and 6. Arrangement 42 includes a half-moon shaped hinge groove 44 formed in section 20 and a half-moon shaped hinge nose 46 extending from section 22, as best shown in FIGS. 4 and 9. Nose 46 is received in groove 44 so that the peripheral surface of the nose slides along the recessed surface of the groove 44 when the cap is pivoted between its open and closed positions. A generally V-shaped relief zone 52 is formed along the top surface of cap 10 when the cap is in its closed position as best shown in FIG. 9. Area 52 is formed by a slanted planar surface 54 of section 20 and a slanted planar surface 56 of section 22. Surface 54 and surface 56 abut against one another when the cap is in its open position to prevent further pivoting of the sections 20 and 22 with respect to each other as best shown in FIG. 6.

An annular channel 58 is formed on the exterior surface of cap 10. One portion of channel 58 is formed on section 20 and the other portion of channel 58 is formed on section 22 as shown in FIG. 4. Channel 58 receives an O-ring 60 which is made of any suitable elastic material, for example, rubber. O-ring 60 is initially stretched outwardly when it is positioned in channel 58. Thus, O-ring 60 applies a biasing force to sections 20 and 22 that tends to hold the two sections together in the closed position of the pull cap.

The exterior surface of cap 10 has a generally annular slanted surface 62. A portion of slanted surface 62 is formed on section 20 and the other portion of slanted surface 62 is formed on section 22 as best shown in FIG. 4. Slanted surface 62 engages a corresponding slanted surface 64 on latch member 16 during the pulling operation, as shown in FIG. 5 and as will be more fully described below. The exterior surface of cap 10 also has a reduced diameter section 66 to allow positioning of latch member 16 around the cap. Further, cap 10 has diametrically opposed planar surfaces 68. Surfaces 68 allow the jaws of a wrench to be positioned around the cap.

In use, cap 10 is pivoted to its open position so that surfaces 28 and 30 are separated from one another as shown in FIG. 6. When cap 10 is in its open position, O-ring 60 is further stretched slightly outwardly thus increasing the biasing force that tends to move sections 20 and 22 to the closed position. Groove 44 and nose 46 are longitudinally positioned along the cap so that these structures are slightly closer to end 70 of the cap than the longitudinal position of channel 58 as shown in FIG. 5. This longitudinal arrangement of groove 44, nose 46, and channel 58 ensures that O-ring 60 will bias the cap to its closed position.

In its open position, the cap is positioned on the exposed end 14 of the probe rod string. Wires or tubes 27 extending out of the central bore of the rod string are generally positioned through the split apart aperture 26 as shown in FIG. 7. In its open position, surfaces 54 and 56 of sections 20 and 22, respectively, abut one another. After the cap has been positioned over end 14, the cap is allowed to close so that the female thread surfaces of sections 20 and 22 engage and surround the male thread surface of end 14 as shown in FIG. 5. In this closed position, aperture 26 completely encircles the wires or tubes 27 extending laterally from the cap. O-ring 60 holds the cap in its closed position.

Latch member 16 is then pivoted so that section 66 of cap 10 is received in C-shaped aperture 72. Pulling device 18 is then actuated upwardly. As latch member 16 is moved upwardly, slanted surface 62 of the cap engages slanted surface 64 of latch member 16 as shown in FIG. 5. This engagement of slanted surfaces 62 and 64 ensures that sections 20 and 22 are secured in the closed position and adequately clasp end 14. After rod section 12 has been removed from the ground, latch member 16 is pivoted away from the cap. The cap is actuated to its open position so that the female thread surfaces of sections 20 and 22 disengage the male thread surface of end 14. Cap 10 can then easily be removed from end 14. Rod section 12 is then disconnected from the rod section below it. The steps above are then repeated for the rod sections remaining in the ground until the probe is removed from the ground.

Cap 10 is designed to allow it to be easily and quickly installed on and removed from the exposed end of a probe rod. More specifically, the positioning of the hinge arrangement adjacent end 70 of the pull cap allows for maximum separation of concave surfaces 28 and 30 when the pull cap is in its open position. Thus, the female thread surfaces on surfaces 28 and 30 are easily positioned about the male thread surface on the end of the probe rod during installation. Further, the female thread surfaces are easily disengaged from the male thread surface of the probe rod section during removal. A user can create the large separation between surfaces 28 and 30 simply by exerting pressure generally at locations 76 and 78 on the exterior surface of the pull cap and adjacent end 70, as best shown in FIGS. 6 and 8. The opening operation can be performed with one hand by simply squeezing the top of the pull cap at locations 76 and 78.

Further, in order to ensure that the pull cap is secured in its closed position during the pulling operation, annular slanted surface 62 is longitudinally positioned remote from the hinge arrangement and adjacent the female thread surface of bore 31. Thus, when latch 16 engages the pull cap, the force exerted by the latch at surface 62 ensures that the cap securely clasps the end of the probe rod section.

In addition to positioning the pull cap on the exposed end of the rod string by actuating it between its open and closed positions, the pull cap can also be positioned on the exposed end simply by threading it thereon while the pull cap is in its closed position. Further, the pull cap can be removed from the exposed end by simply threading it off of the end. Surfaces 68 are provided to engage the jaws of a wrench so that rotation of the cap on and off can be accomplished more easily.

Cap 10 has only three components and is simply and easily manufactured. More particularly, cap 10 is made by first forming an integral body which has a female thread surface defining bore 31. Further, the integral body also has aperture 26 formed in spatial communication with the bore. Channel 58 is also formed on the integral body. Thereafter, the integral body is divided into sections 20 and 22 by a suitable machining process. As part of this machining process, hinge groove 44, hinge nose 46, and relief area 52 are formed. More particularly, a process known as electronic discharge machining can be used to split the body into sections 20 and 22. In this process, the body is placed in deionized water and a very fine charged wire having a high current flowing through it at low voltage is used to cut the piece in half while at the same time forming the hinge structures. After this has been done, O-ring 60 can simply be deformed outwardly so that it surrounds the cap and is received in channel 58. As is apparent, by first forming an integral body and thereafter separating it into sections, it is ensured that the female thread surfaces of sections 20 and 22 will match one another to precisely engage the male thread of the exposed rod end.

Thus, the pull cap of the present invention offers a structure that is easily positioned about and removed from the exposed end of a rod string. Further, the elastic O-ring and the engagement of the annular slanted surface of the cap with the slanted surface of the latch member ensures that the cap is held in its closed position during the pulling operation. Additionally, the cap is able to accommodate rod strings in which wires or tubes are disposed in a central bore of the rod string. The cap is also versatile in that it can be threaded on and off of the exposed end if desired. Still furthermore, the cap is highly advantageous because it consists of a limited number of easily manufactured parts.

Having described the invention, what is claimed is:

1. A pull cap for positioning about the exposed end of a probe rod and for engaging a pulling device to remove the probe rod from the ground, the pull cap comprising:

a first body section having a first concave surface disposed adjacent one end of said first section and for engaging the exposed end of the rod, said first section also having a first channel on its outer surface adjacent the other end of said first section;

a second body section having a second concave surface disposed adjacent one end of said second section and for engaging the exposed end of the rod, said second section also having a second channel on its outer surface adjacent the other end of said second section;

a hinge means disposed on both said first and second sections adjacent said other ends of said first and second sections and for hinging said first and second sections together so that the pull cap can be pivoted between an open position and a closed position, said first and second concave surfaces engaging the exposed end of the probe rod when the pull cap is in its closed position so that the pull cap can be used to remove the probe rod from the ground; and an elastic member positioned in said first and second channels and for biasing the pull cap toward its closed position.

2. The pull cap of claim 1 wherein said hinge means includes:

a hinge groove of generally half-moon cross section formed on said first section; and a hinge nose of generally half-moon cross section formed on said second member and for receipt in said hinge groove, said hinge nose pivoting in said hinge groove to allow the pull cap to pivot between its open and closed positions.

3. The pull cap of claim 2 wherein the longitudinal location of said hinge groove is closer to said other end of said first section than the longitudinal location of said first channel, and wherein the longitudinal location of said hinge nose is closer to said other end of said second section than the longitudinal location of said second channel.

4. The pull cap of claim 2 wherein said elastic member is an O-ring, said O-ring surrounding both said first and second sections to hold said sections together so that said hinge nose is received in said hinge groove.

5. The pull cap of claim 1 wherein said first and second concave surfaces each have a female thread surface, said female thread surfaces enclosing and clasping the exposed end of a probe rod having a male thread surface when the pull cap is moved from its open position to its closed position.

6. The pull cap of claim 1 wherein the pull cap has an outer inclined surface adopted to engage a latch member of a pulling device so that said inclined surface secures the pull cap in its closed position when the latch member applies an upward pulling force to the cap.

7. The pull cap of claim 6 wherein said inclined surface is generally annular in shape, and wherein one half of said inclined surface is formed on said first section and the other half of said inclined surface in formed on said second section.

8. The pull cap of claim 1 wherein said concave surfaces of said first and second sections form a bore that surrounds and clasps the exposed end of the probe rod when the pull cap is moved from its open position to its closed position, the pull cap having an aperture formed on its side surface and in spatial communication with said bore, said aperture formed partially by said first section and partially by said second section so that a wire or tube extending through a central bore in the probe rod can be positioned in the aperture when the pull cap is in its open position and maintained in said aperture when the pull cap is in its closed position.

9. A pull cap for attaching to the upper end of a probe rod to connect a pulling device to the rod for removing the rod from the soil, said cap comprising:

a pair of similar elongated body sections disposed in a mutually facing relationship, each section having an elongated concave surface disposed to face the concave surface of the other section and extending to one end of its corresponding section so that the concave surfaces of both sections jointly define a longitudinally extending bore communicating with one end of the cap through a bore opening;

said sections being configured so that each section provides a respective part of a hinge extending transversely across the cap in spaced relationship from the ends of the sections, the hinge parts cooperating to permit the sections to be manually pivoted about the hinge to swing the bore defining concave surfaces of said sections away from one another, the hinge being disposed substantially closer to the end of the cap remote from the bore opening;

coupling means on at least one of said concave surfaces for engaging the rod to attach the cap to the rod; and means carried by the sections and engagable by the pulling device for holding said sections against swinging away from one another during pulling of the rod from the ground.

10. The pull cap of claim 9 wherein a relief zone extends between the hinge and the end of the cap remote from said bore opening when said bore is formed by said concave surfaces, said relief zone being defined by a pair of mutually facing surfaces, each of said body sections having one of said facing surfaces, said facing surfaces moving towards one another as said body sections are pivoted about said hinge to swing the bore defining concave surfaces of said sections away from one another.

11. The pull cap of claim 10 wherein said relief zone is generally V-shaped.

12. The pull cap of claim 9 further comprising biasing means disposed adjacent the end of the cap remote from said bore opening and for biasing said concave surfaces towards one another, said biasing means being disposed at a longitudinal location that is closer to said boring opening than said hinge.

* * * * *